United States Patent [19]

Lederer et al.

[11] Patent Number: 5,430,434

[45] Date of Patent: Jul. 4, 1995

[54] PORTABLE SURGICAL EARLY WARNING DEVICE

[76] Inventors: Gabor Lederer, 28 Summit Ave., Hackensack, N.J. 07601; Cal Rifkin, 647 Klondike Ave., Staten Island, N.Y. 10314

[21] Appl. No.: 22,004

[22] Filed: Feb. 24, 1993

[51] Int. Cl.[6] .......................................... G08B 21/00
[52] U.S. Cl. .................................. 340/540; 340/647; 128/897; 128/917
[58] Field of Search ............... 340/540, 647, 573, 650, 340/648, 657; 128/638, 846, 844, 918, 897, 898, 917, 918, 642; 324/557, 559, 636, 263, 631

[56] References Cited

U.S. PATENT DOCUMENTS

| | | | |
|---|---|---|---|
| 4,909,069 | 3/1990 | Albin et al. | 340/540 |
| 4,956,635 | 9/1990 | Langdon | 340/540 |
| 5,036,309 | 7/1991 | Dennison, Jr. | 340/540 |
| 5,109,215 | 4/1992 | Dennison | 340/540 |

*Primary Examiner*—Brent Swarthout
*Assistant Examiner*—Benjamin C. Lee
*Attorney, Agent, or Firm*—Israel Nissenbaum

[57] ABSTRACT

A portable early warning device for use in detection of breaches in protective garments such as gloves, during surgical procedures and the like. The device embodies a central process and source unit containing sensing wave generator, indicators, driving circuitry, digital analyzing and monitoring circuitry and a power source. The central process and source unit is separately directly connected to the object, e.g. skin of the patient, and to the device carrier, e.g. skin of the surgeon, via standard wires and EKG type terminal connectors. A conductive breach of protective garments such as surgical gloves with in vivo patient fluids, such as blood (of a possibly hazardous nature), completes a circuit and triggers a warning (either visible, audible, or mechanical) of the breach. The driving and monitoring circuitry, which generates a pulse specific current, prevents spurious signals despite the heightened sensitivity required by the device for triggering and the presence of numerous electronic devices, with emitting electrical discharges, which are present in operating rooms. The device is provided with self diagnostic monitoring means to ensure proper over-all hook-up; separate proper connection to each of the surgeon and patient; sufficient battery power; and proper operation.

7 Claims, 4 Drawing Sheets

PORTABLE SURGICAL EARLY WARNING DEVICE

FIELD OF THE INVENTION

This invention relates to devices utilized in detection of breaches of personal protective barriers by electrically conductive fluids, such as body fluids. The invention relates particularly to detection of breaches of personal protective gloves during surgical procedures.

BACKGROUND OF THE INVENTION

Surgical procedures are fraught with the possibility of infectious contact of surgical personnel with body fluids, particularly the blood of patients. Surgical gowns and gloves are designed to provide protection. However, exigencies of the situation, particularly with the use of sharp instruments, contact with bone, application of excessive pressure and necessarily thin gloves can occasionally lead to unnoticed pinholes, rips, etc. in the protective garment. This leads to the ingress of possibly infectious body fluids into direct contact with the surgical personnel. The prevalence of AIDS and HIV has most recently exacerbated such concern. Expedients to alleviate such concern generally encompass the use of pin-hole detection devices which provide immediate warning of a breach to allow for immediate effective action.

An example of such warning device is disclosed in U.S. Pat. No. 4,956,635 in which a circuit, interrupted by the surgical gloves, is established between surgeon and patient. A reference external electrical circuit is established on the surgeon, wherein a breach in the glove barrier results in a measurable voltage drop which triggers an alarm warning. However, spurious signals can be triggered, such as by static electric charge build-ups and discharges, which generate a sufficient voltage.

Interruptions in surgical procedures resulting from spurious signals are costly and possibly harmful.

SUMMARY OF THE INVENTION

It is an object of the present invention to provide a personal barrier breach signal device not susceptible to spurious signals.

It is a further object of the present invention to provide such device without the necessity of establishing a reference electrical circuit.

It is a still further object of the present invention to provide such device wherein the overall connection and the separate connections to patient and to surgeon are constantly checked.

It is another object of the present invention to provide protection for any number of health care workers with the same patient at the same time without electrical interference between devices.

These and other objects, features and advantages of the present invention will become more evident from the following discussion and drawings in which:

SHORT DESCRIPTION OF THE DRAWINGS

DETAILED DESCRIPTION OF THE INVENTION

Figure 1:
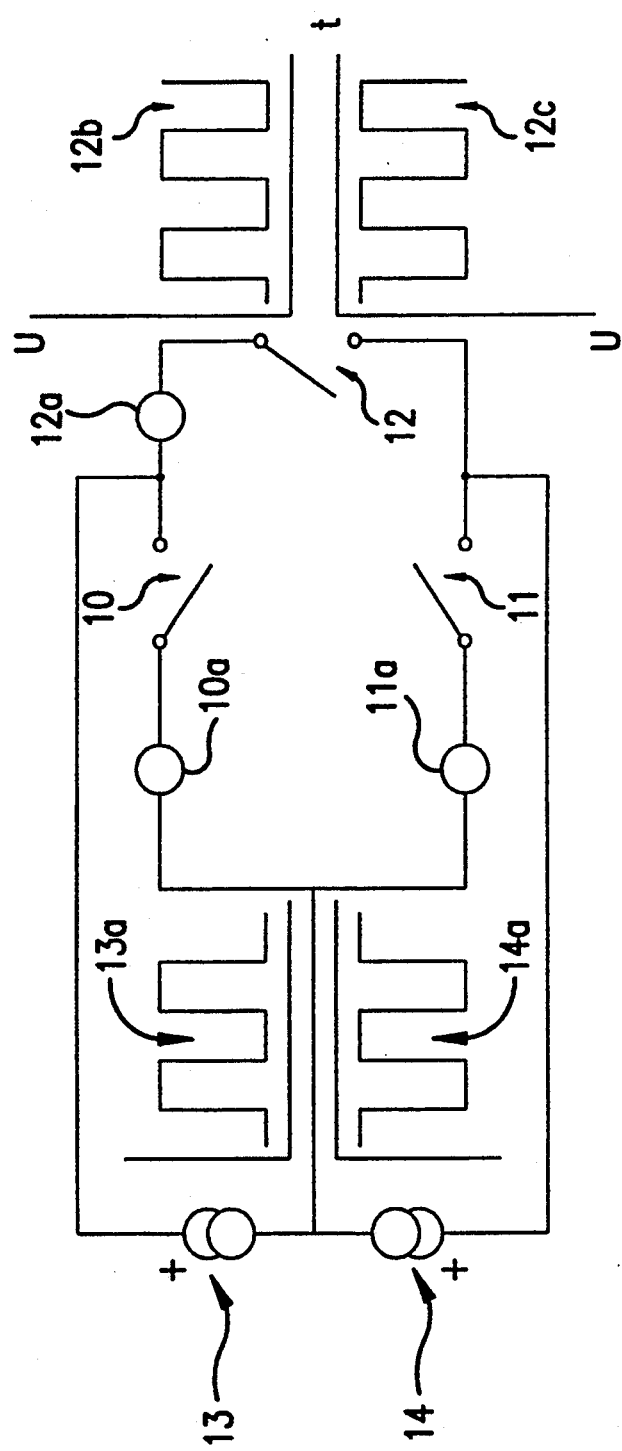
FIG. 1 is a simplified electrical circuitry illustrating the triple check circuitry and breach check circuitry respectively of the present invention.

Generally the present invention comprises an early warning device for use in detection of a breach in at least one protective barrier between an object and the carrier, during surgical and health care procedures. The device is separately electrically connected, with individual connections to the object and the carrier, said device comprising alarm means, central processing means, and means to constantly monitor integrity of each connection during use of the device. Any failed connection condition causes the alarm means to generate an alarm as to such condition to enable the failed connection condition to be corrected. With a breach in the protective barrier, and establishment of a conductive connection between the object and carrier, a circuit is completed through the device with a current generation, and a warning alarm is triggered by the alarm means. The device further comprises discrimination means wherein said alarm is only triggered when the discrimination means determines that the generated current is of a specific predetermined type.

More specifically the present invention comprises a portable early warning device for use in detection of breaches in protective garments such as gloves, during surgical procedures and the like. The device is electrically connected to an object (e.g. patient) and to a carrier (e.g. a surgeon and/or health care worker) and comprises electrical pulse generation means and central processing means whereby electrical pulses, continually generated by the electrical pulse generation means, are separately directed to the surgeon and the patient, to monitor integrity of each connection during use of the device. A failed connection provides an alarm as to such condition to enable it to be corrected. With a barrier breakdown, such as a hole in a surgical glove, and establishment of a conductive fluid connection with in vivo patient fluids, such as blood (of a possibly hazardous nature), a circuit is completed between the surgeon and patient, and through the device, and a warning alarm is triggered. Such alarm is however only triggered when the central processing means determines that a generated current is of a pulse type and is of the specific pulse rate generated by the pulse generation means. The pulse generations for the patient and surgeon are preferably identical but phase shifted so that they are separately identifiable. With the completion of the circuit between surgeon and patient, the pulses are shunted to the breach alarm circuit and combined. It is this combined pulse rate which is detected and analyzed by the central processing means.

The pulse generation and rate detection eliminates any spurious signals with unwanted alarm triggering. The device senses only the presence or absence of the pre-established signal and is analogous to a switch being open and closed. Secondary source changes in resistance levels, as is possible with prior art devices, are not a factor in alarm triggering. In addition, several devices may be hooked up to a single patient for protection of other health care workers, without danger of cross signals.

The alarm may be in the form of visual, audio or tactile indications, e.g. a blinking warning light, a sounding buzzer or beep, or a detectable vibratory movement. In a preferred embodiment, means are provided for a remote perception of the alarm near the surgeon's eyes or ears. Separate alarm indicators inform the user of low battery condition and loss of connection integrity from either the surgeon or patient connection.

In a preferred embodiment of a device of the present invention, the device embodies a central process and source unit containing sensing wave or pulse generator, indicators, driving circuitries, digital analyzing and monitoring circuitries and a power source. The device is separately directly connected to the object, e.g. skin of the patient, and to the device carrier, e.g. skin of the surgeon, via standard two conductor wires and EKG type dual electrodes. The driving and monitoring circuitries, which generates a pulse specific current, prevents spurious signals despite the heightened sensitivity required by the device for triggering and the presence of numerous electronic devices, with emitting electrical discharges, which are present in operating rooms. The device is provided with self diagnostic monitoring means to ensure proper over-all hook-up; separate proper connection to each of the surgeon and patient; sufficient battery power; and proper operation.

DETAILED DESCRIPTION OF THE DRAWINGS AND THE PREFERRED EMBODIMENT

Figure 4:
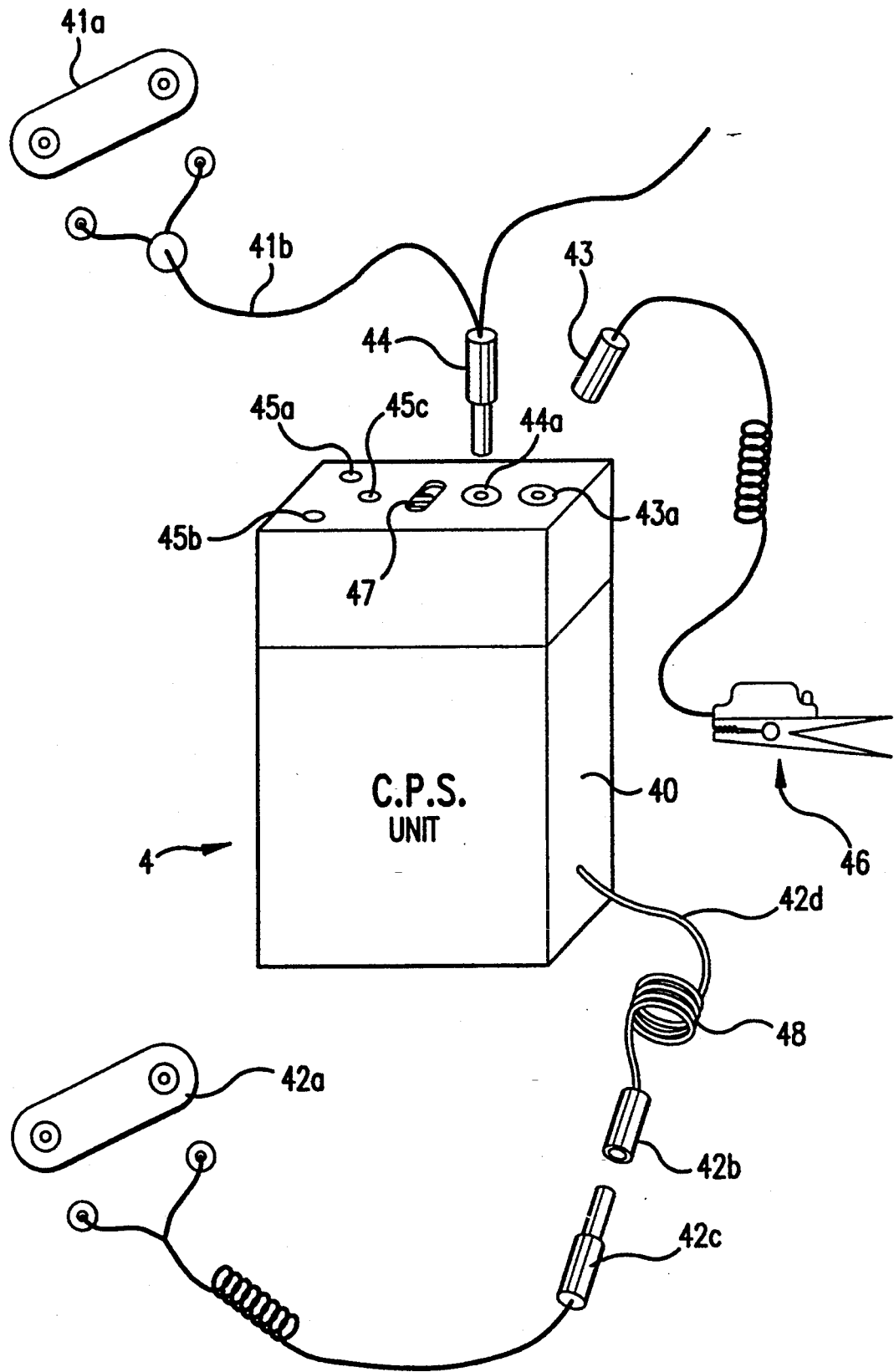
FIG. 4 is an isometric view of the device of the present invention shown with various connective elements.

With specific reference to the drawings, FIG. 1 depicts a schematic of the circuitry used in the present invention to detect a breakdown in the connection cable to the carrier (surgeon) or the object (patient) or a breach of a protective barrier such as a glove. Switch 10 represents the condition of a connection established on the carrier. A proper connection is indicated with a closure of switch 10 and lighting of light emitting diode (LED) 10a, to indicate integrity of the connection to the carrier. Similarly, switch 11 represents the condition of a connection established on the object. A proper connection is indicated by closure of switch 11 and lighting of LED 11a, to indicate integrity of the connection to the object. Switch 12 represents integrity of a protective barrier. A breakdown or breach of the barrier is indicated by closure of the switch and lighting of LED 12a. During operation of the device, pulse signal generators 13 and 14, connected in series, generate pulses 13a, 14a, 12b, and 12c. Connection integrity LEDs 10a and 11a can be combined in a single signal LED as shown in FIG. 4 as LED 45b.

Figure 2:
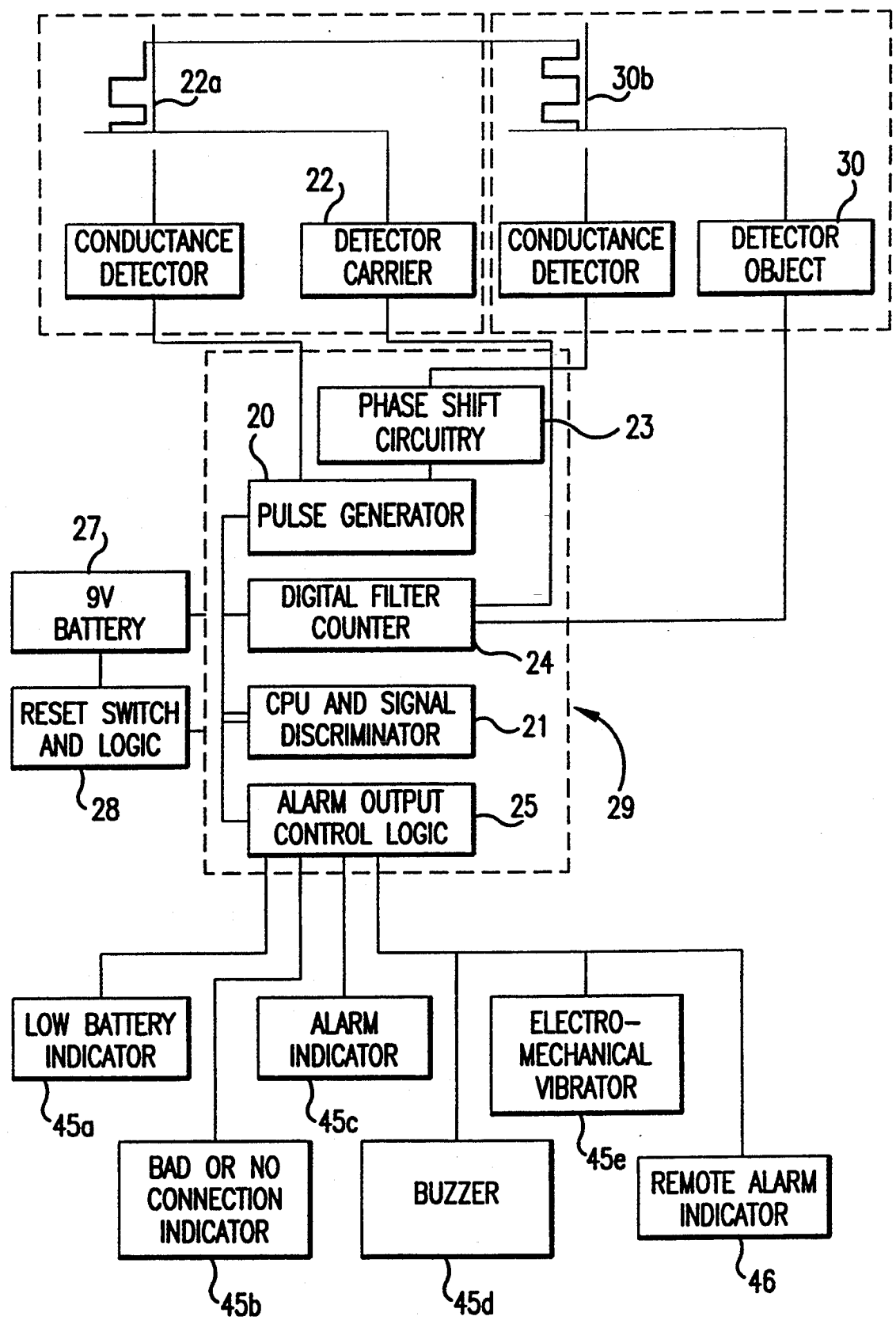
FIG. 2 is a block diagram with operative elements of the device of the present invention and the specific connections for detection of malfunctions and/or breaches.

FIG. 2, illustrates the device circuitry, which contains a microcontroller 29, defined by the dashed lines. The microcontroller is comprised of pulse generator 20 and a central processing unit (CPU) 21. The pulse generator 20 continually emits electrical pulses 22a as a conductance detector for the detector carrier 22 and separate, phase shifted pulses 30b, through the phase shift logic 23, as a conductance detector for the detector object 30. The returned signals, returned through digital filter and counter 24, are separately recognized by the CPU 21 because of the phase shift, whereby both electrical connections to carrier 41 and object 42 are separately continually checked for integrity.

With a break in any of the circuits to carrier 41 or object 42, or a breach in protective gear which completes a circuit between carrier and object, a signal is sent to alarm output control logic element 25 to determine whether the electrical signal matches that of an alarm condition, and the signal is from 22a or 30b or the combination of the two inputs, e.g. a preprogrammed pulse rate. If there is a match, the appropriate indicator or alarm is activated by logic element 25.

The device is powered by a typical 9 volt battery 27 and the state of the battery is monitored wherein a low battery condition causes the alarm output control logic element 25 to trigger low battery indicator 45a.

Figure 3:
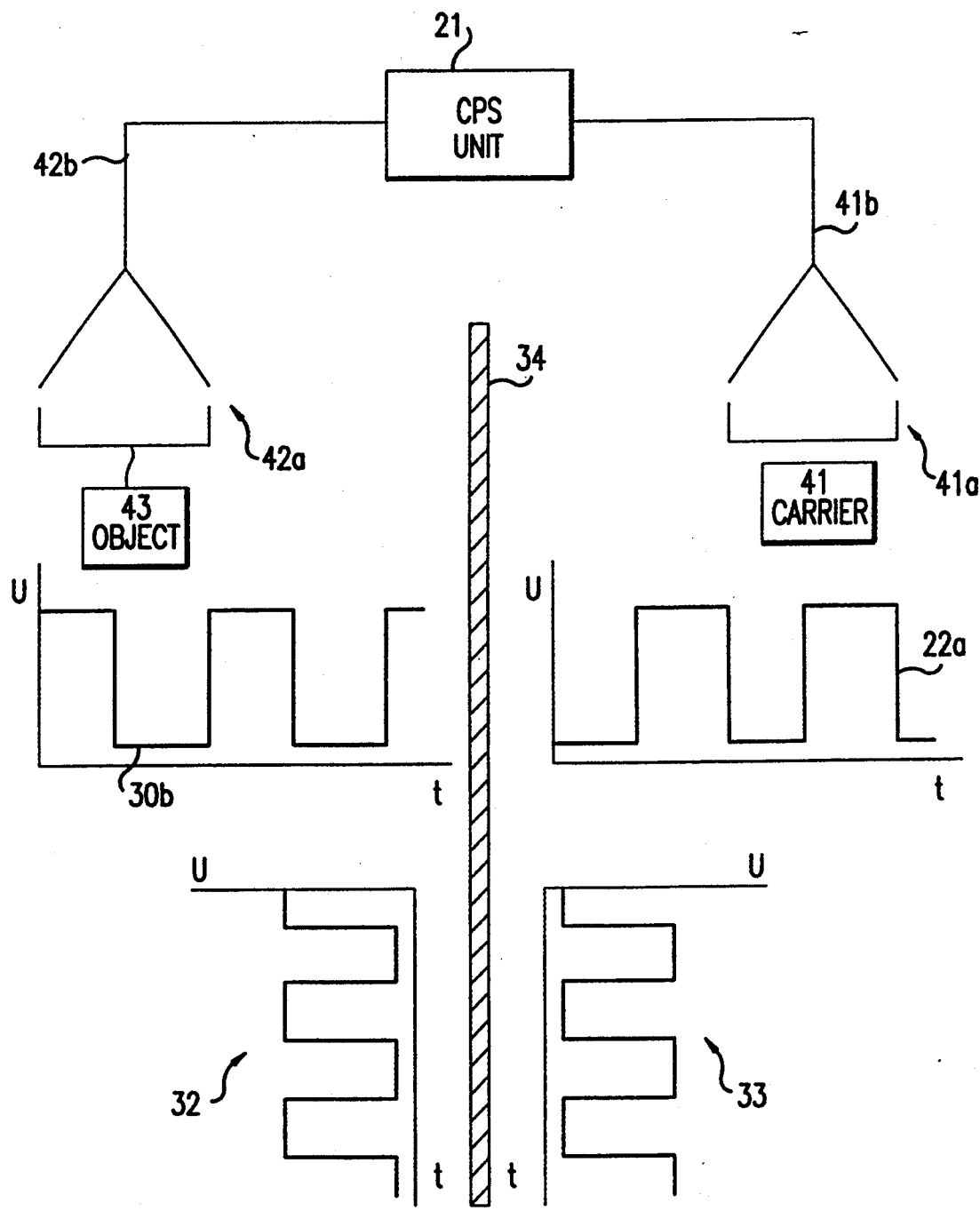
FIG. 3 illustrates the phase shifted pulse generation of the device for monitoring object (patient) and carrier (surgeon) connection integrity, and breach of barrier.

FIG. 3 depicts the relation of generated pulses, with reference to the microprocessor controlled circuitry, to both the carrier 41 and the object 42 relative to the central processor unit 21 with separation by barrier 34, e.g. a surgical glove. As shown in FIG. 3, the pulse generator emits counted pulses 32 to the object 42 (e.g. patient) and if there is no receiving of the pulses, the connection is defective and an alarm is triggered. In order to filter out extraneous noise and static charges the number of pulses within a cycle are counted in filter and counter unit 24. These pulse signals 30b start at time 1 as a positive high signal. The pulses 22a emitted by the pulse generator to the carrier (e.g. surgeon) 41 are identical to pulses 30b but at time 1 has a "0" low value resulting from the phase shift.

With a breakdown of barrier 34, the CPU 21 receives a continuously low signal as a summation of pulses. The phase shifted signals, upon a barrier breach, will trigger the alarm circuitry and in their individual form also continuously monitor the integrity of the connections. In order to enhance sensitivity, it is preferred that the gloves be lined with a conductive material such as graphite or carbon which facilitates generation of the alarm circuit.

In FIG. 4, a warning device 4, comprised of a housing 40 with contained circuitry, schematically set forth in FIG. 2, is provided with external dual wire connections 41b and 42d which are connected to EKG type dual electrode pads 41a and 42a respectively, affixed to the skin of the surgeon 41 and patient 42 respectively. The wire connection 42d, having a wire spring coil 48, terminates in receptacle 42b for connection with connector 42c, which is, in turn connected with EKG type pad 42a.

Warning light signals 45a; 45c and 45b on the device, are light emitting diodes (LEDs) which are respectively separately illuminated, with a low voltage condition (indicating a need for battery replacement) and an overall warning light if there has been a breach in the protective garments of the surgeon such as a hole in a surgical glove or if there has been a disconnection to either the surgeon or patient. For additional, warnings remote unit 46, with self contained buzzer and light is plugged, by connector 43 into socket 43a. The remote unit is then clipped onto clothing adjacent the surgeon's ears or eyes for facilitated recognition of a device warning. Reset switch 47 permits re-set of the device after an alarm has been triggered.

In operation mode, warning light signal 45a indicates that the battery has insufficient charge. The warning light signal 45a will flash if the battery is close to discharge. Warning light signal 45c will blink if there is a barrier breakdown between the patient and surgeon and/or health care worker. Warning signal 45c will continue blinking, even with rectification of the breach, until the unit 4 is reset with reset switch 47. In addition to warning signal 45c, buzzer 45d and mechanical indicator 45e will be activated (a buzzer and mechanical vibrator, contained within the housing (not shown), to provide additional audio and tactile warnings). In addition, there is activation of remote unit 46 and its contained remote light and buzzer unit, to ensure that the breach of protective barrier is noticed.

Warning light signal 45b is constantly off, with a proper connection condition with respect to both the connections to the patient and the surgeon. Should the integrity of any connection be compromised, warning light signal 45b will blink until the condition is rectified. With all of the warning signals, a blinking condition is indicative of a need to take some action; replacement of barrier garment, change of battery, or rectification of disconnection condition.

It is understood that the above description and drawings illustrate a preferred embodiment of the present invention and that changes in components, objects (the object can be the glove itself in a pre-operation test), carriers (e.g. carriers can also be secondary personnel in an operating room setting), connections, circuitry and the like can be made without departing from the scope of the present invention as defined in the following claims.

What is claimed is:

1. An early warning portable, battery powered device for use in detection of a breach in at least one protective barrier between an object and at least one carrier, during surgical and health care procedures, wherein the device contains a battery power source and is separately electrically connected, with individual connections, to the object and at least one carrier by dual electrode cables, said device comprising central processing means having discrimination means, connection integrity alarm means, breach alarm means, and means to constantly monitor integrity of each connection during use of the device, with said connection integrity alarm means, said breach alarm means, and said means to constantly monitor integrity of each connection, each being electrically connected to said central processing means, wherein any failed connection condition causes the connection integrity alarm means to generate an alarm as to such condition to enable the failed connection condition to be corrected, and wherein, with a breach in said protective barrier, and establishment of a conductive connection between the object and said at least one carrier, a circuit is completed through the breach with a current generation from said battery power source, and a warning alarm is triggered by the breach alarm means; said discrimination means, being electrically connected to said breach alarm means and said current generation, wherein said warning alarm is only triggered when the discrimination means determines that the generated current is of a specific predetermined type, wherein said device further comprises electrical pulse generation means whereby electrical pulses, continually generated by the electrical pulse generation means, are separately directed to the object and the at least one carrier respectively, to monitor integrity of each connection during use of the device, wherein the electrical pulses, separately directed to the object and the at least one carrier respectively, differ such that they provide said generated current of specific predetermined type, identifiable by said discrimination means.

2. An early warning-portable, battery powered device for use in detection of a breach in at least one protective barrier between an object and at least one carrier, during surgical and health care procedures, wherein the device contains a battery power source and is separately electrically connected, with individual connections, to the object and at least one carrier by dual electrode cables, said device comprising central processing means with discrimination means, connection integrity alarm means, breach alarm means, and means to constantly monitor integrity of each connection during use of the device, with said connection integrity alarm means, said breach alarm means, and said means to constantly monitor integrity of each connection, each being electrically connected to said central processing means, wherein any failed connection condition causes the connection integrity alarm means to generate an alarm as to such condition to enable the failed connection condition to be corrected, and wherein, with a breach in said protective barrier, and establishment of a conductive connection between the object and said at least one carrier, a circuit is completed through the breach with a current from said battery power source, and a warning alarm is triggered by the breach alarm means; said current being generated by pulse current generation means; said discrimination means being electrically connected to said breach alarm means and said current generation, wherein said warning alarm is only triggered when the discrimination means determines that the generated current is of a specific predetermined type, wherein said discrimination means determines that said generated current is of a pulse type having a specific predetermined pulse rate generated by the pulse generation means, with the electrical pulses directed to each of said object and the at least one carrier, being substantially identical in height and rate, but phase shifted so that they are separately identifiable, and wherein with the completion of the circuit, the pulses to the object and to the at least one carrier are shunted to the breach alarm means and combined, with the combined pulses comprising the pulse type having the specific predetermined pulse rate.

3. The device of claim 2, wherein said barrier comprises a surgical glove, said object comprises a patient and said carrier comprises a surgeon.

4. The device of claim 3, wherein said surgical glove comprises a conductive powder material which facilitates establishment of the conductive connection.

5. The device of claim 2, wherein said device further comprises low battery alarm means, electrically connected to said battery, wherein a low remaining battery capacity causes the low battery alarm means to trigger an alarm.

6. The device of claim 2, wherein said device further comprises remote alarm and said warning alarm as indications of failed connection integrity and breach of the protective barrier respectively, wherein said remote alarm is connected, in series with said warning alarm, to said central processing means.

7. The device of claim 2, wherein said alarm comprises a flashing light and wherein said warning alarm comprises at least one of a flashing light, a buzzer and a mechanical vibration.

* * * * *